(12) United States Patent
Zuccolo et al.

(10) Patent No.: US 9,326,927 B2
(45) Date of Patent: May 3, 2016

(54) USE OF CANNABINOID COMPOUNDS FOR STIMULATING MELANOGENESIS

(75) Inventors: Michela Zuccolo, Paris (FR); Roland Jourdain, Meudon (FR); Lionel Breton, Versailles (FR); Mauro Maccarrone, L'Aquila (IT)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/237,015

(22) PCT Filed: Aug. 3, 2012

(86) PCT No.: PCT/FR2012/051846
§ 371 (c)(1),
(2), (4) Date: Feb. 20, 2014

(87) PCT Pub. No.: WO2013/021128
PCT Pub. Date: Feb. 14, 2013

(65) Prior Publication Data
US 2014/0193349 A1    Jul. 10, 2014

(30) Foreign Application Priority Data
Aug. 5, 2011    (FR) ..................... 11 57213

(51) Int. Cl.
| | | |
|---|---|---|
| A61K 8/42 | (2006.01) |
| A61Q 5/10 | (2006.01) |
| A61Q 19/04 | (2006.01) |
| A61K 31/164 | (2006.01) |
| A61K 31/16 | (2006.01) |
| A61Q 5/00 | (2006.01) |
| A61Q 19/00 | (2006.01) |

(52) U.S. Cl.
CPC . *A61K 8/42* (2013.01); *A61K 31/16* (2013.01); *A61K 31/164* (2013.01); *A61Q 5/00* (2013.01); *A61Q 5/10* (2013.01); *A61Q 19/00* (2013.01); *A61Q 19/04* (2013.01)

(58) Field of Classification Search
None
See application file for complete search history.

(56) References Cited

U.S. PATENT DOCUMENTS

| | | | |
|---|---|---|---|
| 2002/0182159 A1* | 12/2002 | McGlone et al. | ............... 424/65 |
| 2008/0262079 A1 | 10/2008 | Mach et al. | |
| 2010/0249080 A1 | 9/2010 | Burry et al. | |
| 2011/0301078 A1 | 12/2011 | Schetz et al. | |

FOREIGN PATENT DOCUMENTS

| | | | |
|---|---|---|---|
| CA | 2463282 | * | 5/2003 |
| EP | 0 355 842 | | 2/1990 |
| FR | 2 848 106 | | 6/2004 |
| WO | 95-11003 | | 4/1995 |
| WO | 2006-024958 | | 3/2006 |
| WO | 2009-071422 | | 6/2009 |
| WO | 2009-158499 | | 12/2009 |

OTHER PUBLICATIONS

Magina, Sofia et al., "Inhibition of basal and ultraviolet B-induced melanogenesis by cannabinoid CB1 receptors: a keratinocyte-dependent effect", Archives of Dermatological Research., vol. 303, No. 3, pp. 201-210, XP055026334, 2011.
International Search Report Issued Apr. 16, 2013 in PCT/FR12/051846 Filed Aug. 3, 2012.

* cited by examiner

*Primary Examiner* — Robert A Wax
*Assistant Examiner* — Melissa Mercier
(74) *Attorney, Agent, or Firm* — Oblon, McClelland, Maier & Neustadt, L.L.P.

(57) ABSTRACT

The invention relates to the nontherapeutic cosmetic use of at least one cannabinoid compound chosen from the compounds corresponding to general formula (I):

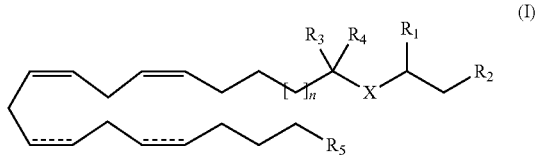

and also the geometric isomers and optical isomers thereof, the cosmetically acceptable acid or base salts thereof, and the hydrates thereof;
in which compounds of formula (I):
- $R_1$ represents a hydrogen atom or a $C_1$-$C_{30}$ alkyl group; it being possible for said alkyl group to be optionally substituted with a hydroxyl (OH) group;
- $R_2$ represents a halogen atom or a group chosen from hydroxyl, thiol (SH), and amino optionally substituted with one or two $C_1$-$C_6$ alkyl groups;
- $R_3$ and $R_4$ form, together with the carbon atom which bears them, an oxo group or else $R_3$ and $R_4$ represent a hydrogen atom;
- $R_5$ represents a hydrogen atom or a $C_1$-$C_6$ alkyl group;
- X represents a heteroatom chosen from oxygen and sulfur atoms and the divalent group —N($R_6$)—, with $R_6$ representing a hydrogen atom or a $C_1$-$C_6$ alkyl group;
- ---- represents a single or double bond;
- n is 1, 2 or 3, preferentially 1 or 2;

it being understood that, when $R_3$ and $R_4$ together form an oxo group with the carbon atom which bears them and X represents an oxygen atom, then $R_1$ cannot represent a hydroxymethyl group, as an agent for coloring keratin materials. It also relates to one of these specific cannabinoid compounds for use thereof in the treatment of vitiligo or *pityriasis versicolor*, to nontherapeutic cosmetic processes for coloring the skin or for treating canities, comprising the topical application to the skin and/or head hair, or the oral administration, of a composition comprising, in a physiologically acceptable medium, one of these cannabinoid compounds, and to a process for selecting an active agent which promotes the pigmentation of keratin materials.

15 Claims, 2 Drawing Sheets

USE OF CANNABINOID COMPOUNDS FOR STIMULATING MELANOGENESIS

The present invention relates to the cosmetic and/or dermatological use of cannabinoid compounds, in a composition for coloring and/or pigmenting the skin and/or body hair and/or head hair.

The color of human hair and skin depends on various factors and in particular the seasons of the year, ethnic origin, sex and age. It is mainly determined by the concentration, in the keratinocytes, of melanin produced by the melanocytes. Melanocytes are specialized cells which, by means of particular organelles, the melanosomes, synthesize melanin. This melanin synthesis, or melanogenesis, is the result of the interaction between α-MSH (α-melanocyte stimulating hormone) and its receptor MC1R (melanocortin receptor type 1), which interaction activates a signalling cascade that induces the tyrosinase enzyme via the MITF transcription factor.

Melanogenesis is particularly complex and schematically involves the following main steps:

Tyrosine→Dopa→Dopaquinone→Dopachrome→Melanin

Tyrosinase (monophenol dihydroxyl phenylalanine: oxygen oxidoreductase/EC 1.14.18.1) is the essential enzyme involved in this sequence of reactions. In particular, it catalyzes the conversion reaction of tyrosine to give Dopa (dihydroxyphenylalanine) and the conversion reaction of Dopa to give dopaquinone.

In the epidermis, the melanocyte is involved in the epidermal melanin unit which comprises a melanocyte surrounded by approximately 36 neighbouring keratinocytes. All individuals, without phototype distinction, have approximately the same number of melanocytes for a given area of skin. Ethnic differences, in terms of pigmentation, are not due to the number of melanocytes, but to the properties of their melanosomes. Melanosomes are aggregated in complexes and are small in size. They are highly specialized organelles, the sole function of which is melanin production. They arise from the endoplasmic reticulum in the form of spherical vacuoles called premelanosomes. Premelanosomes contain an amorphous protein substrate, but no melanogenic enzymes. During maturation of the premelanosome, the amorphous substrate is organized into a fibrillar structure oriented along the longitudinal axis of the melanosome. Four stages of development of the melanosome are distinguished, corresponding to the intensity of the melanization. Melanin is deposited uniformly on the internal fibrillar network of the melanosome and the opacity of the organelle increases until saturation occurs. As the melanin is synthesized in the melanosomes, the latter move from the perinuclear region to the end of the melanocyte dendrites. By means of phagocytosis, the end of the dendrites is taken up by the keratinocytes, the membranes are degraded and the melanosomes are redistributed in the keratinocytes.

Nowadays, it is important to look healthy, and a tanned skin is always a sign of good health. However, a natural tan is not always desirable since it requires prolonged exposure to UV radiation, in particular to UV-A radiation. This radiation causes tanning of the skin but, on the other hand, it is liable to induce an adverse change therein, in particular in the case of sensitive skin or of continual exposure to solar radiation. The skin ages prematurely, becomes dry and is characterized by numerous wrinkles and senescence marks. It is thus desirable to find an alternative to a natural tan that is compatible with the requirements of such skin types.

The search for pigmenting compounds is also of interest in the treatment of pigmentation diseases, for instance vitiligo, which is an autoimmune disease characterized by the appearance on the skin of white patches associated with a pigmentation defect, or else *pityriasis versicolor* caused by the yeast *Malassezia furfur* (marks which may be achromatic immediately or after exposure to the sun).

Another pigmentation defect is the appearance of white hairs in human beings (canities or natural whitening of hair) which can be either a visible manifestation of the aging process (senile canities), or linked to a genetic predisposition. The pigmentation of head hair and of body hair requires the presence of melanocytes in the bulb of the hair follicle. It is now accepted that canities is associated with a decrease in the amount of melanin in the hair shaft. Since maintaining a constant coloration of the head of hair is a sizeable aspiration, it is therefore desirable to be able to combat the appearance of these visible signs of aging, i.e. to maintain or re-establish the coloration of body hair and/or of head hair.

It would thus be particularly advantageous to have novel means for facilitating and/or improving the pigmentation of the skin and/or of body hair and/or of head hair in the dermatology and cosmetic field. These novel means would in particular be useful for preventing and/or limiting and/or stopping the development of canities and even maintaining the natural pigmentation of gray or white head hair and/or body hair.

There is therefore a real need for a product which facilitates and/or improves the pigmentation of the skin and/or of body hair and/or of head hair.

Many solutions have been proposed in the artificial coloring field.

In the exogenous coloring agent field, dihydroxyacetone, or DHA, is a particularly advantageous product which is commonly used in cosmetics as an artificial skin-tanning agent. When applied to the skin, in particular to the face, it makes it possible to obtain a tanning or browning effect that is similar in appearance to that which can result from prolonged exposure to the sun (natural tan) or under a UV lamp.

Erythrulose is also a substance that is used for the same purpose. These compounds act by binding to the amino acids, peptides and proteins of the stratum corneum, according to the Maillard reaction (nonenzymatic reaction between a sugar and an amine).

These colorations obtained with compounds of self-tanning type as previously defined appear after a few hours but disappear quite rapidly, and are not always homogenously distributed on the skin.

In order to obtain colorations which last over time, it has been proposed in the prior art to act directly on the biological process of melanogenesis by means of α-MSH or prostaglandins, so as to stimulate melanin biosynthesis, with or without the action of UV radiation. For example, documents WO 95/17161, WO 95/11003, WO 95/01773, WO 94/04674, WO 94/04122, EP 0 585 018, WO 93/10804, WO 92/20322 and WO 91/07945 have proposed solutions as varied as compositions containing an inhibitor of phosphodiesterases, of prostaglandins, DNA fragments or else tyrosine derivatives.

Although it was thought that there was no other melanogenesis pathway that does not depend on α-MSH and MC1R, the applicant has discovered, surprisingly, that some cannabinoid compounds make it possible to induce melanin biosynthesis and to obtain a more homogeneous and long-lasting skin coloration than when exogenous coloring agents are used. The new pathway described results in a faster pigmentation. Moreover, this natural pigmentation is physiologically more effective than a synthetic pigment.

For the purposes of the present invention, the term "cannabinoid compound" is intended to mean any simple or complex substance or compound of natural or synthetic origin, which activates the cannabinoid receptors present in the body and in particular in the skin. There are three major categories thereof: plant cannabinoids or phytocannabinoids, endogenous cannabinoids or endocannabinoids, and synthetic cannabinoids produced in laboratories.

Endocannabinoids are active lipids which act as CB1 and CB2 receptor ligands. These receptors belong to the G protein-coupled transmembrane receptor superfamily. The CB1 receptor is encoded by the CNR1 gene present on chromosome 6. One of the main endocannabinoids is anandamide or AEA (N-arachidonoylethanolamine). The synthesis of AEA is dependent on the N-acylphosphatidylethanolamine (NAPE)-specific phospholipase D (NAPE-PLD) enzyme, while its degradation takes place via hydrolysis by the FAAH (fatty acid amide hydrolase) enzyme. Methanandamide or mAEA (R(+)-arachidonyl-1'-hydroxy-2'-propylamide) is a nonhydrolyzable analog of AEA and is, like AEA, a CB1, CB2 and TRPV1 receptor agonist ligand. Arachidonyl-2'-chloroethylamide ou ACEA is also an AEA analog and is equally a CB1 receptor agonist ligand. The entry of endocannabinoids into the cell is saturable and energy-dependent, and it takes place via the endocannabinoid membrane transporter (EMT).

AEA and the proteins which bind to this compound, transport it, synthesize it and hydrolyze it are part of the endocannabinoid system (ECS). Endocannabinoids have been identified, both in humans and in mice, in a large number of cell types of the skin and of the associated structures, such as epidermal keratinocytes, dermal mast cells, sebocytes and the epithelium of the hair follicle (Maccarrone et al, J Biol Chem, 2003, Dobrosi et al., FASEB J, 2008). It has been shown that the components of the ECS control the proliferation, differentiation, apoptosis and cytokine production of skin cells, which suggests that this system has a role in epidermal homeostasis. Moreover, the binding of agonist ligands such as AEA to cannabinoid receptors in the skin leads to a reduction in inflammatory processes, whereas antagonists worsen inflammatory skin episodes such as in pathological conditions of allergic dermatitis type.

Anandamide has already been described for its antibacterial (WO 2009/158499), pain-killing or else anti-inflammatory effects, in particular via the vanilloid receptor signalling pathways. However, it has never been described as acting on melanocytes or as being able to have an effect on the production of melanin via cannabinoid receptors as in the present invention.

Magina et al. (Arch Dermatol Res. 2011) describes an inhibition of melanogenesis following the exposure of cocultures of keratinocytes and melanocytes to UV radiation. The melanocytes used in these cocultures are distinctive since they are in this case human melanoma cells, i.e. cancer cells.

The authors put forward the hypothesis that this effect on melanogenesis is due to the action of endocannabinoid mediators secreted by the keratinocytes and acting on the surrounding melanocytes. The applicant has therefore gone against what is suggested in this publication, by testing cannabinoid receptor ligands for their melanogenesis-stimulating effect.

A subject of the present invention is thus the cosmetic (nontherapeutic) use of at least one CB1 receptor activator, preferentially at least one CB1 receptor activator with the exception of 2-arachidonoylglycerol (2-AG) alone (i.e. when the 2-AG is not associated with another CB1 receptor activator), as an agent for coloring keratin materials.

Figure 1:
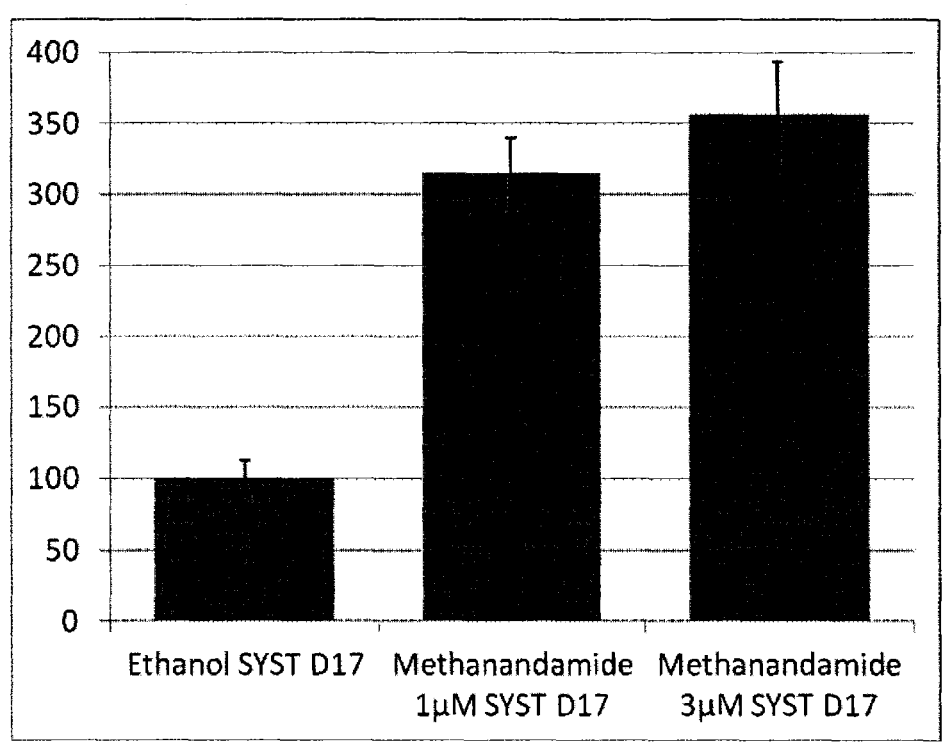
FIG. 1 depicts the results of the evaluation of the propigmenting effect of mAEA on pigmented reconstructed epidermises from Example 3.

A CB1 receptor activator is, according to the present invention, any simple or complex substance or compound of natural or synthetic origin which binds to the CB1 receptor and induces a biological response similar to that which is obtained with the natural ligand of this receptor which activates this response or which increases the release and/or synthesis of endocannabinoids. This characteristic of these compounds can be easily verified using methods known to those skilled in the art, namely respectively using a method for measuring selective receptor affinity (referred to as "binding" method) coupled to a measurement of the functional activity of said compound or of said substance (see in particular J. Med. Chem. 2007, 50, 3851-3856) or using a method of controlled release of endocannabinoids (referred to as "release" method).

The CB1 receptor activator can be chosen preferentially from CB1 receptor agonist ligands or endocannabinoid release inducers (otherwise known as "release" inducers) and more preferentially from CB1 receptor agonist ligands and even more preferentially from CB1 receptor agonist ligands with the exception of 2-arachidonoylglycerol (2-AG) alone (i.e. when the 2-AG is not associated with another CB1 receptor agonist ligand).

For the purposes of the present invention, the term "endocannabinoid release inducers" is intended to denote any simple or complex substance or compound of natural or synthetic origin which induces the endogenous synthesis and/or release of endocannabinoids. They are also called functional agonists.

A CB1 receptor agonist ligand is, according to the present invention, any simple or complex substance or compound of natural or synthetic origin which will bind to a cannabinoid receptor present in the human body, in particular to the CB1 receptor, and which will induce a biological response similar to that which is obtained with the natural ligand of this receptor which activates this response.

The CB1 receptor agonist ligands are preferentially chosen from cannabinoid compounds, anandamide and its analogs, in particular methanandamide, arachidonyl-2'-chloroethylamide, linoleyl ethanolamide, noladin ether, CP 55,940 ([(−)-cis-3-[2-hydroxy-4-(1,1-dimethylheptyl)phenyl]-trans-4-(3-hydroxypropyl)-cyclohexanol]), O-2050 [(6aR,10aR)-3-(1-methanesulfonylamino-4-hexyn-6-yl)-6a,7,10,10a-tetrahydro-6,6,9-trimethyl-6H-dibenzo[b,d]pyran], and mixtures thereof.

These agonists are capable of browning or darkening keratin materials and/or of improving and/or accelerating and/or restoring the coloration or the pigmentation of keratin materials and in particular of the skin and/or of head hair.

Preferentially, a subject of the present invention is the nontherapeutic cosmetic use of at least one cannabinoid compound chosen from the compounds corresponding to general formula (I):

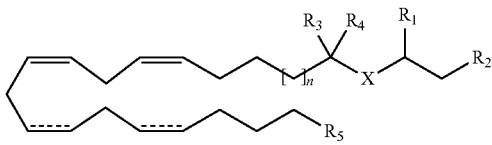

and also the geometric isomers (cis/trans or Z/E) and optical isomers (enantiomers) thereof, the cosmetically acceptable acid or base salts thereof, and the hydrates thereof such as the solvates;

in which compounds of formula (I):
- $R_1$ represents a hydrogen atom or a $C_1$-$C_{30}$ alkyl group, preferentially a $C_1$-$C_6$ alkyl group, even more preferentially a methyl group; it being possible for said alkyl group to be optionally substituted with a hydroxyl (OH) group;
- $R_2$ represents a halogen atom or a group chosen from hydroxyl, thiol (SH), and amino optionally substituted with one or two $C_1$-$C_6$ alkyl groups, more particularly chosen from a halogen, such as chlorine, and a hydroxyl group;
- $R_3$ and $R_4$ form, together with the carbon atom which bears them, an oxo group or else $R_3$ and $R_4$ represent a hydrogen atom;
- $R_5$ represents a hydrogen atom or a $C_1$-$C_6$ alkyl group such as methyl or ethyl;
- X represents a heteroatom chosen from oxygen and sulfur atoms and the divalent group —N($R_6$)—, with $R_6$ representing a hydrogen atom or a $C_1$-$C_6$ alkyl group;
- ---- represents a single or double bond;
- n is 1, 2 or 3, preferentially 1 or 2;

it being understood that, when $R_3$ and $R_4$ together form an oxo group with the carbon atom which bears them and X represents an oxygen atom, then $R_1$ cannot represent a hydroxymethyl group, as an agent for coloring keratin materials.

The term "keratin material" is intended to mean the skin (of the face, of the body, of the scalp), head hair, the eyelashes, the eyebrows and the nails. The term "keratin material" is preferentially intended to mean the skin and/or head hair.

The term "coloring agent" is intended to mean any substance or compound capable of browning or darkening keratin materials and/or of improving and/or promoting and/or accelerating and/or restoring the coloration or the pigmentation of keratin materials.

This cannabinoid compound is preferentially chosen from anandamide (AEA) and analogs thereof. The term "analog" compounds is intended to mean compounds of synthetic or natural origin having a chemical structure analogous to anandamide and which are capable of binding to the same receptors. In particular, the anandamide analogs are chosen from methanandamide (mAEA), arachidonyl-2'-chloroethylamide (ACEA), linoleyl ethanolamide, docosatetraenyl ethanolamide and 2-arachidonyl glyceryl ether (2-AGE, noladin ether).

AEA, mAEA and ACEA, linoleyl ethanolamide, docosatetraenyl ethanolamide and 2-arachidonyl glyceryl ether, of similar chemical structure, have the following chemical formulae (the abbreviation =O signifies oxo group, dl signifies "double bond" and sl signifies "single bond"):

| | $R_1$ | $R_2$ | $R_3$ and $R_4$ | $R_5$ | X | $R_6$ | ---- | n |
|---|---|---|---|---|---|---|---|---|
| Anandamide | H | OH | O | $C_2H_5$ | N($R_6$) | H | dl | 1 |

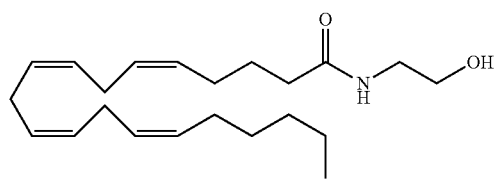 [SMILES: CCCCC/C=C\C/C=C\C/C=C\C/C=C\CCCC(=O)NCCO]

| | | OH | O | $C_2H_5$ | N($R_6$) | H | dl | 1 |
|---|---|---|---|---|---|---|---|---|

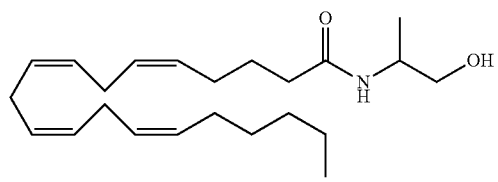 [SMILES: CCCCC/C=C\C/C=C\C/C=C\C/C=C\CCCC(=O)NC(C)CO]

| | | | | | | | | |
|---|---|---|---|---|---|---|---|---|
| Arachidonyl-2'-chloroethylamide | H | | O | $C_2H_5$ | N($R_6$) | H | dl | 1 |

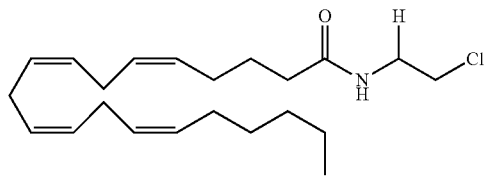 [SMILES: CCCCC/C=C\C/C=C\C/C=C\C/C=C\CCCC(=O)NCCCl]

| Structure | $R_1$ | $R_2$ | $R_3$ and $R_4$ | $R_5$ | X | $R_6$ | ---- | n |
|---|---|---|---|---|---|---|---|---|
| (arachidonoyl ethanolamide structure) | | | OH | O | H | $N(R_6)$ | H | 1 |
| (docosahexaenoyl ethanolamide structure) | H | | OH | O | $C_2H_5$ | $N(R_6)$ | H | dl | 2 |
| (arachidonoyl 2-chloro-1-hydroxymethyl structure) | | O H | $CH_3$ substituted with OH | OH | O | $C_2H_5$ | O | H | dl | 1 |

The browning or the darkening of the skin or the improving, the accelerating or the restoring of the coloration or of the pigmentation can be assessed visually or using methods of physical measurement of the coloration of the skin or of head hair, which are well known to those skilled in the art (in particular using the colorimetric measurement system (L*, a*, b*)).

The CB1 receptor agonist ligand or the cannabinoid compound as defined above can be present in a composition at a concentration of between 0.00001% and 10% by weight, preferably between 0.001% and 5% by weight and in particular between 0.01% and 1% by weight, relative to the total weight of the composition.

Preferentially, the CB1 receptor activator or the cannabinoid compound, as defined above, is used as an agent for increasing the pigmentation of keratin materials and/or for stimulating melanogenesis, in particular by means of CB1 receptor activation, and/or as a skin-browning agent and/or as an artificial skin-tanning agent.

By virtue of this use, the skin will appear darker, more brown, more tanned and/or more rapidly tanned.

The term "artificial tanning" is intended to mean browning, darkening or increased pigmentation of the skin not directly linked to exposure to the sun or to UVA and/or UVB radiation. The browning obtained will be close to natural tanning.

The term "natural tanning" is intended to mean browning, darkening or increased pigmentation of the skin directly linked to exposure to the sun or to UVA and/or UVB radiation.

More particularly, the CB1 receptor activator or the cannabinoid compound, as defined above, is used according to the invention as an agent for slowing or treating canities or the natural whitening of head hair. Through the use of a CB1 receptor activator or of a cannabinoid compound according to the invention, it is in particular possible to maintain and/or re-establish the natural pigmentation of head hair and/or of body hair.

The term "treating" is also intended to mean preventing, reducing or slowing.

The invention also relates to a cannabinoid compound or a CB1 receptor activator, as defined above, for use thereof in the treatment of a dermatological complaint which has a dyschromic component, such as vitiligo or *pityriasis versicolor*. It is also directed toward the use of at least one CB1 receptor activator or one cannabinoid receptor, as defined above, for preparing a composition intended for treating any dermatological complaint which has a dyschromic component, such as vitiligo or *pityriasis versicolor*.

The expression "dermatological complaint which has a dyschromic component" is intended to mean any complaint, disease or pathological condition in which abnormal pigmentation (preferentially insufficient pigmentation) is observed on a part or on all of the skin of an individual.

The composition for the use according to the invention is in particular appropriate for topical application or appropriate for oral administration and contains, moreover, a physiologically acceptable medium. The CB1 receptor activators or the cannabinoid compounds according to the invention, alone or as a mixture, and also the composition comprising them, can be used by topical application to keratin materials or by oral administration. The composition can in particular be a cosmetic composition or a dermatological composition.

The term "appropriate for topical application" or "appropriate for oral administration" is intended to mean, respectively, "suitable for topical application" or "suitable for oral administration".

According to the invention, the term "physiologically acceptable medium" is intended to mean a cosmetically or pharmaceutically acceptable medium which is compatible with the skin (including the scalp), head hair, the mucous membranes and/or the eyes.

The term "cosmetically acceptable medium" is intended to mean a medium that has no unpleasant odor or appearance, and that does not cause the user any unacceptable stinging, tautness or redness when it is applied topically to the skin or skin appendages.

The physiologically acceptable medium will be adapted to the nature of the support onto which the composition is to be applied, and also to the form in which the composition is intended to be packaged, in particular solid or fluid at ambient temperature and atmospheric pressure.

The composition may also comprise all the usual cosmetic additives, such as water, solvents, oils, waxes, pigments, fillers, surfactants, cosmetic or dermatological active agents, UV-screening agents, polymers, gelling agents, preservatives and fragrances.

Needless to say, a person skilled in the art will take care to select this or these optional additional compound(s), and/or the amount thereof, such that the advantageous properties of the compounds according to the invention are not, or are not substantially, adversely affected by the envisioned addition.

The composition according to the invention can be in all the formulation forms normally used in the cosmetics and dermatology fields; it can in particular be in the form of an aqueous, aqueous-alcoholic or oily solution, which is optionally gelled, of a dispersion of the lotion type, optionally comprising two phases, of an oil-in-water or water-in-oil or multiple emulsion, of an aqueous or oily gel, of a liquid, pasty or solid anhydrous product, of a dispersion of oil in an aqueous phase using spherules, it being possible for these spherules to be polymeric nanoparticles, such as nanospheres and nanocapsules, or better still lipid vesicles of ionic and/or nonionic type.

Another subject of the invention is a nontherapeutic cosmetic process for coloring or pigmenting the skin, comprising the topical application to the skin, or the oral administration, of a composition comprising, in a physiologically acceptable medium, a cannabinoid compound or a CB1 receptor activator, as defined above.

Preferentially, this cosmetic process is a skin-browning process or an artificial skin-tanning process.

The invention also relates to a nontherapeutic cosmetic process for treating canities, comprising the topical application to head hair, or the oral administration, of a composition comprising, in a physiologically acceptable medium, a cannabinoid compound or a CB1 receptor activator, as defined above.

In one or other of these processes, the CB1 receptor activator or the cannabinoid compound can be present at a concentration of between 0.00001% and 10% by weight, relative to the total weight of the composition, preferably between 0.001% and 5% by weight and in particular between 0.1% and 1% by weight.

One or other of these cosmetic methods may comprise a single application or administration. According to a particular embodiment, the application or administration is repeated, for example, 2 to 3 times daily over one day or more, and generally over an extended period of at least 4 weeks, or even 4 to 15 weeks, with, where appropriate, one or more periods of interruption.

Another subject of the invention is a process for selecting an active agent which promotes the pigmentation of keratin materials, comprising:

a) a step of preselection of a CB1 receptor activator, b) a step of final selection of a CB1 receptor activator preselected in the previous step, as an active agent which promotes the pigmentation of keratin materials, when the amount of melanin produced by melanocytes placed in contact with said activator is greater than that produced by melanocytes which have not been in contact with this CB1 receptor activator.

The CB1 receptor activator is as defined above. It may be a CB1 receptor agonist ligand or an endocannabinoid release inducer, the CB1 receptor agonist ligand being preferentially chosen from cannabinoid compounds corresponding to formula (I), as defined above.

The CB1 receptor agonist or activator nature of a compound or of a substance is evaluated using any method known to those skilled in the art, in particular using a method for measuring selective receptor affinity (referred to as "binding" method) coupled to a measurement of the functional activity of said compound or of said substance (see in particular J. Med. Chem. 2007, 50, 3851-3856) or using a method of controlled release of endocannabinoids (referred to as "release" method).

The selective receptor affinity measurement can be carried out by bringing CB1 receptors (or cell membranes comprising these receptors) into contact with labeled ligands (e.g. radiolabeled, immunofluorescent, etc., ligands), by removing the labeled ligands which have not bound to the receptors and by determining the amount of labeled ligands which have bound to the receptors.

The measurement of the functional activity of a compound or of a substance in order to validate its CB1 receptor agonist nature can be carried out by measuring the amount of cyclic AMP (cAMP) produced by a cell culture (i.e. a culture of melanocytes or a coculture of melanocytes and keratinocytes or a pigmented reconstructed epidermis or a skin explant), following the addition of forskolin and of said compound or of said substance. If a decrease in the amount of cAMP is observed following the addition of the compound or of the substance, then its CB1 receptor agonist or activator nature is validated. Cyclic AMP is in fact one of the known compounds of which the synthesis is inhibited following activation of the CB1 receptor. Forskolin is known to increase cAMP synthesis.

A method of controlled release of endocannabinoids will be carried out by bringing a compound or a substance into contact with a cell culture (i.e. a culture of melanocytes or a coculture of melanocytes and keratinocytes or a pigmented reconstructed epidermis or a skin explant) and by measuring the amount of endocannabinoids produced.

In step b), the amount of melanin produced by melanocytes can be measured on a culture of melanocytes or on a coculture of melanocytes and keratinocytes or on a pigmented reconstructed epidermis or on a skin explant. In step b), the CB1 receptor activator preselected in step a) can be added, at a predetermined concentration, to one or other of these cell cultures and the amount of melanin produced by the melanocytes present in these cultures is measured. A controlled measurement is carried out on one or other of these cell cultures without having added CB1 receptor activator.

The final selection of a CB1 receptor activator as an active agent which promotes the pigmentation of keratin materials in step b) of the selection process is carried out by comparing the amount of melanin produced by melanocytes brought into contact with said CB1 receptor activator and the amount of melanin produced by melanocytes which have not been brought into contact with said CB1 receptor activator. A CB1 receptor activator can thus be selected as an active agent which promotes the pigmentation of keratin materials, if it increases by at least 10%, preferentially by at least 20%, and even more preferentially by at least 30%, the amount of melanin produced by melanocytes which have not been in contact with said CB1 receptor activator.

The conditions for culturing melanocytes alone or in coculture with keratinocytes and also the methods for preparing a pigmented reconstructed epidermis (see in particular EP 1 878 790) or a skin explant are known to those skilled in the art.

The measurement of the amount of melanin produced by melanocytes, optionally in coculture with keratinocytes or present in pigmented reconstructed epidermidis or in a skin explant, is carried out according to methods known to those skilled in the art (see, for example, Xiao et al., Arch Dermatol Res 2007; 299: 245-57). Preferentially, this measurement is carried out by spectrophotometry and even more preferentially by spectrophotometry at 450 nm.

Another subject of the invention is a process for selecting an agent for coloring keratin materials or an active agent which promotes the pigmentation of keratin materials, comprising:

a) a step of bringing a test product (P) into contact with melanocytes, b) a step of measuring the amount of melanin produced by the melanocytes, c) a step of comparing the amount of melanin measured in step b) with the amount of melanin (i) produced by melanocytes which have been brought into contact with the product (P) and a compound which inhibits CB1 receptor activity, d) a step of comparing the amount of melanin measured in step b) with the amount of melanin (ii) produced by melanocytes which have not been in contact either with the product (P) or with a compound which inhibits CB1 receptor activity, e) a step of selecting a product (P) as an agent for coloring keratin materials or an active agent which promotes the pigmentation of keratin materials, when the amount of melanin measured in step b) is significantly greater than the amount of melanin (ii) and the amount of melanin (i) is not significantly different than the amount of melanin (ii), the conditions for measuring the amount of melanin being the same in steps a, b, c and d.

The bringing of the test product (P), optionally combined with a compound which inhibits CB1 receptor activity, into contact with melanocytes is preferentially carried out by bringing these compounds into contact with a culture of melanocytes, a coculture of melanocytes and keratinocytes, a pigmented reconstructed epidermidis or a skin explant.

For the purposes of the invention, the term "compound which inhibits CB1 receptor activity" is intended to mean any simple or complex substance or compound of natural or synthetic origin which is capable of inhibiting or reducing the activity of the CB1 receptor, and therefore which will prevent its effects from being produced. This term can therefore denote, for example, anandamide-degrading enzymes (if there is no more ligand available, there is no more activation). This term therefore also denotes any molecular substance or means (interfering RNA, siRNA, miRNA) capable of specifically inhibiting the expression of the receptor itself.

Those skilled in the art will very easily identify the inhibiting nature of a substance or of a compound using the methods for measuring the activity of a receptor which are known to those skilled in the art. An example of such a method is given in the document Endocrinology 2009; 150:4692-4700.

As a compound which inhibits CB1 receptor activity, mention may be made of N-piperidino-5-(4-chlorophenyl)-1-(2,4-dichlorophenyl)-4-methyl-3-pyrazole carboxamide), also known under the names SR1, SR141716 or rimonabant and in particular sold by the company Sigma Aldrich, or under the brand name Acomplia™ or Zimulti™ sold by the company Sanofi Aventis.

The amount of compound which inhibits CB1 receptor activity that can be used is determined in such a way that the CB1 receptor activity is reduced by 80%, preferentially 90% and even more preferentially 100%. By way of example, 0.1 µM of SR1 can be used to totally inhibit CB1 receptor activity.

One or other of these selection processes makes it possible to specifically select products which can be used as agents for promoting the coloration of the skin and/or of body hair and/or of head hair. These products have the particularity of stimulating melanogenesis or pigmentation of the skin and/or of body hair and/or of head hair, by means of CB1 receptor activation.

In the description and in the examples that follow, unless otherwise mentioned, the percentages are weight percentages and the ranges of values written in the form "between . . . and . . . " include the stated lower and upper limits. The ingredients are mixed, before being formed, in the order and under conditions that can be readily determined by those skilled in the art.

EXAMPLE 1

Demonstration of the Propigmenting Effect of 3 Cannabinoid Compounds

1. Materials and Methods
1.1. Compounds Tested

Anandamide (AEA) and methanandamide (mAEA) are supplied by Sigma Chemical Co. (St. Louis, Mo.). Arachidonyl-2'-chloroethylamide (ACEA) is supplied by Cayman Chemical (Ann Arbor, Mich.).

1.2. Reagents Used

The compounds SR1=N-piperidino-5-(4-chlorophenyl)-1-(2,4-dichlorophenyl)-4-methyl-3-pyrazole carboxamide (specific CB1 receptor antagonist) and SR2=N-[(1S)-endo-1,3,3-trimethy-1-bicyclo[2.2.1]heptan-2-yl]-5-(4-choro-3-methylphenyl)-1-(4-methylbenzyl)pyrazole-3-carboxamide (specific CB2 receptor antagonist, also called SR144528) are supplied by Sanofi-Aventis Recherche (Montpellier, France).

1.3. Cell Culture and Treatment

Normal human epidermal melanocytes (NHEMs) isolated from foreskins and supplied by Promocell (Heidelberg, Germany) are cultured for 24 h at 37° C. in a humid atmosphere at 5% $CO_2$ in an appropriate culture medium M2 (Promocell).

The AEA and the other compounds are added directly to the culture medium. Twenty-four hours after each treatment, the cell viability was measured using Trypan blue exclusion dye (Maccarone et al., 2003).

The mAEA, the AEA and the ACEA are tested in vitro at a concentration of 1 µM and compared. The mAEA is also used at this concentration when it is used in combination with SR1 at 0.1 µM.

Moreover, the mAEA was also tested, alone, at concentrations of 0.5, 1.0, 1.5, 2.0, 2.5 and 3.0 µM.

1.4. Determination of the Melanin Content of the Melanocytes

The amount of melanin present in the NHEM cells is measured according to a method known to those skilled in the art (Xiao et al., Arch Dermatol Res 2007; 299: 245-57). According to this method, the NHEM cells are treated with trypsin and washed twice with a phosphate buffered saline. The samples are then resuspended in 200 µl of MilliQ water, and 1 ml of an ethanol: ether mixture (1:1, vol/vol) is added in order to remove the opaque substances other than melanin. After 15 minutes, the samples are centrifuged at 600 g for 5 minutes. The pellet is air-dried and dissolved in 200 µl of 1 N sodium hydroxide. The samples are then heated at 80° C. for one hour and cooled.

The amount of melanin is determined by spectrophotometry at 450 nm using the standard melanin controls supplied by Sigma Chemical Co., so as to verify the linearity range of the test. The amount of melanin is expressed relative to the control.

1.5. Statistical Analysis

The results given are the means, with their standard deviations, of 3 independent tests, each carried out in triplicate. They were compared by analysis of variance (ANOVA).

2. Results 2.1. Demonstration of the Propigmenting Effect of the Compounds Tested

|  | Control |  |  |  |  |  |
|---|---|---|---|---|---|---|
| Mean | 1.10 | 2.80 | 2.09 | 2.14 | 1.22 | 2.34 |
| Standard deviation (SD) | 0.10 | 0.26 | 0.22 | 0.21 | 0.09 | 0.30 |
| Standard Error (SEM) | 0.06 | 0.15 | 0.13 | 0.12 | 0.05 | 0.17 |

***p < 0.001 vs control

Anandamide and its two analogs, mAEA and ACEA, significantly increase the amount of melanin in the melanocytes (NHEMs) by means of the CB1 receptor. The mechanism of action by means of the CB1 receptor is demonstrated in the light of the results obtained using SR1 in combination with methanandamide: it is in fact observed that a specific CB1 receptor antagonist, such as SR1, prevents mAEA from having its propigmenting effect. SR2, which is a specific CB2 receptor antagonist, does not, on the other hand, prevent mAEA from having this effect.

2.2. Demonstration of the Dose/Effect Relationship for mAEA

|  | Control | 0.5 | 1*** | 1.5*** | 2*** | 2.5*** | 3*** |
|---|---|---|---|---|---|---|---|
| Mean | 1.02 | 1.75 | 2.80 | 3.30 | 3.34 | 3.75 | 4.13 |
| Standard deviation (SD) | 0.08 | 0.20 | 0.26 | 0.26 | 0.50 | 0.19 | 0.41 |
| Standard error (SEM) | 0.04 | 0.12 | 0.15 | 0.15 | 0.29 | 0.11 | 0.23 |

***p < 0.001 vs control

It was clearly demonstrated that mAEA induces a dose-dependent increase in melanin production in the NHEM cells.

2.3. Conclusions

Given these results, anandamide and its two analogs mentioned above can therefore be effectively used for promoting coloration of the skin and/or of body hair and/or of head hair. By increasing the melanin contents in the skin or in head hair, these compounds thus mimic the natural coloration of these keratin materials.

EXAMPLE 2

Cosmetic Compositions

Propigmenting Cream

| Ingredients | Amounts (in grams) |
|---|---|
| Anandamide | 5.00 |
|  | 7.00 |
| Glyceryl stearate | 2.00 |

-continued

| Ingredients | Amounts (in grams) |
|---|---|
| Cetyl alcohol | 1.50 |
| Polydimethylsiloxane | 1.50 |
| Liquid paraffin | 15.00 |
| Glycerol | 20.00 |
| Preservatives | qs |
| Demineralized water | qs 100.00 g |

After application of this cream to the skin, an increase in the skin coloration is observed.

Hair Lotion

| Ingredients | Amounts (in grams) |
|---|---|
|  | 0.50 |
| Propylene glycol | 30.00 |
| Ethyl alcohol | 40.50 |
| Water | qs |

After application of this lotion to a head of hair containing white hairs, a decrease in the natural whitening of the hair is observed.

EXAMPLE 3

Evaluation of the Propigmenting Effect of mAEA on Pigmented Reconstructed Epidermises (PREs)

Pigmented epidermises are reconstructed on a collagen support (BPER [biodressing for reconstructed epidermis]) using normal human melanocytes and keratinocytes.

The epidermises are obtained after 8 days of reconstruction; the melanocytes chosen are of estimated phototype IV.1.

Some epidermises are treated daily with the placebo, others with the test product mAEA at different concentrations (1 µM and 3 µM).

Each experimental condition is performed in quadruplicate.

The histological quality of the epidermises after treatment is evaluated on histological sections after HES staining in order to determine the impact of the treatment on the epidermises. Also, the physiology of the melanocytes is studied in order to detect any melano-cytotoxicity. If no histological modification nor any melanotoxic effect of the product evaluated is noted, the pigmentation is quantified by quantifying the melanin on histological sections by image analysis.

Analysis of the Results

Quantification of the pigmentation by microscopic quantification of the melanin is then carried out and makes it possible to illustrate a propigmenting activity of the test compound.

The melanin present in the epidermis is stained on histological sections (Fontana Masson staining) and then quantified by image analysis. For this, each epidermis is photographed over its entire width using a microscope. Approximately 10 images are acquired per epidermis (white light, ×20 magnification).

The area taken up by melanin is quantified using custom-designed image analysis software. Briefly, each image is segmented into 4 zones according to their color (lumen, stratum corneum, live epidermis and BPER). The melanin present in the epidermis in the form of black granules is thresholded as being the darkest zone of the epidermis from the red point of view. The pixels occupied by the melanin in the whole epidermis or the live layers are then quantified.

This quantification takes into account the area taken up by the melanin and also the average localization of the melanin in the epidermis.

The results below are expressed as percentage relative stimulation with respect to the control cultured in standard coculture medium.

TABLE 1

| compound tested | % | value |
|---|---|---|
| Ethanol SYST D17 | 100 | 12.5 |
| Methanandamide 1 µM SYST D17 | 315 | 25 |
| Methanandamide 1 µM SYST D17 | 356.25 | 37.5 |

The results are presented in FIG. 1.

It is observed that mAEA induces a very large increase in melanin production in the pigmented reconstructed epidermidises, in a dose-dependent manner.

EXAMPLE 4

Evaluation of the Propigmenting Effect on NHEMs or NHEMs-NHEKs

Primary human melanocytes (NHEMs) were seeded into 24-well plates in the presence (coculture) of normal human epidermal keratinocytes (NHEKs) and then cultured for 24 h. The cells were then treated with nothing (negative control), IBMX (positive control, 200 µM), or methanandamide (mAEA, 1 µM).

After treatment, the cells were incubated for 72 h, all the experimental conditions having been carried out in triplicate.

After 72 h of incubation, the cells were lysed with a 0.5 N NaOH solution in order to extract the melanin.

Quantification of the pigmentation by microscopic quantification of the melanin is then carried out and makes it possible to illustrate a propigmenting activity of the test compound.

The optical density of the samples was measured at 405 nm, with reference to an exogenous melanin range (standard melanin curve 0.39 to 100 µg/ml).

Figure 2:
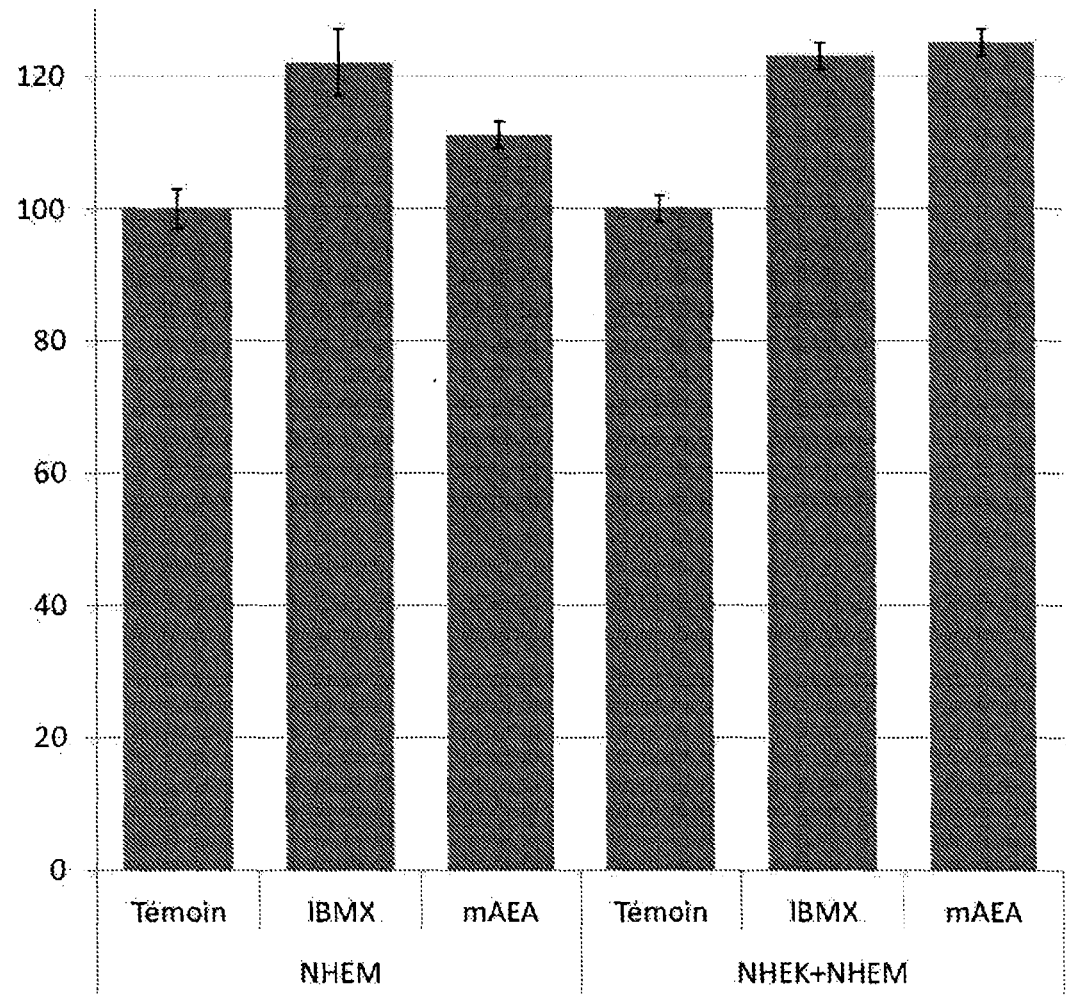
FIG. 2 depicts the results of the evaluation of the propigmenting effect on NHEMs or NHEMs-NHEKs from Example 4.

The results are presented in FIG. 2.

It is observed that mAEA induces an increase in melanin production in the NHEM cells and also in the NHEK+NHEM cells. The melanin production in NHEKs+NHEMs is greater than in NHEMs alone, even exceeding that of the IBMX positive control.

The invention claimed is:

1. A process for coloring a keratin material comprising:
   treating a keratin material in need of coloring with a composition comprising a coloring effective amount of at least one cannabinoid compound selected from the group consisting of a compound of formula (I):

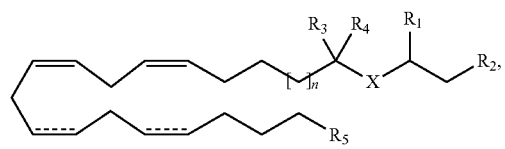

(I)

a geometric isomer thereof, an optical isomer thereof, a cosmetically acceptable acid or base salt thereof, and a hydrate thereof;

wherein:
   $R_1$ represents a hydrogen atom, or a $C_1$-$C_{30}$ alkyl group, which is optionally substituted with a hydroxyl (OH) group;
   $R_2$ represents a halogen atom or a group selected from the group consisting of a hydroxyl group, a thiol (SH) group, and an amino group optionally substituted with one or two $C_1$-$C_6$ alkyl groups;
   $R_3$ and $R_4$ form an oxo group via carbon atoms of $R_3$ and $R_4$ or else $R_3$ and $R_4$ represent a hydrogen atom;
   $R_5$ represents a hydrogen atom or a $C_1$-$C_6$ alkyl group;
   X represents a heteroatom selected from the group consisting of oxygen and sulfur, and a divalent group of —N($R_6$)—, with $R_6$ representing a hydrogen atom or a $C_1$-$C_6$ alkyl group;
   ---- represents a single or double bond; and
   n is 1, 2 or 3;
   with the proviso that, when $R_3$ and $R_4$ form an oxo group via carbon atoms of $R_3$ and $R_4$ and X represents an oxygen atom, $R_1$ is not a hydroxymethyl group.

2. The process of claim 1, wherein the cannabinoid compound is selected from the group consisting of anandamide, methanandamide, arachidonyl-2'-chloroethylamide, linoleyl ethanolamide, docosatetraenyl ethanolamide and 2-arachidonyl glyceryl ether.

3. The process of claim 1, wherein the cannabinoid compound is an agent for increasing pigmentation of the skin and/or body hair and/or head hair.

4. The process of claim 1, wherein the cannabinoid compound is a skin-browning agent.

5. The process of claim 1, wherein the cannabinoid compound is an agent for slowing natural whitening of head hair.

6. The process of claim 1, wherein the cannabinoid compound is an agent for stimulating melanogenesis.

7. A cannabinoid compound, which is a compound of formula (I):

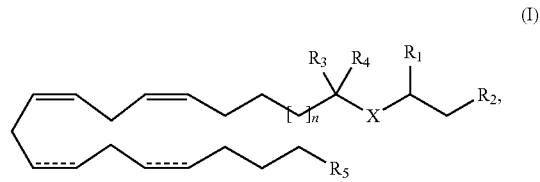

(I)

a geometric isomer thereof, an optical isomer thereof, a cosmetically acceptable acid or base salt thereof, or a hydrate thereof, wherein
   $R_1$ represents a hydrogen atom, or a $C_1$-$C_{30}$ alkyl group, which is optionally substituted with a hydroxyl (OH) group;
   $R_2$ represents a halogen atom or a group selected from the group consisting of a hydroxyl group, a thiol (SH) group, and an amino group optionally substituted with one or two $C_1$-$C_6$ alkyl groups;
   $R_3$ and $R_4$ form an oxo group via carbon atoms of $R_3$ and $R_4$ or else $R_3$ and $R_4$ represent a hydrogen atom;
   $R_5$ represents a hydrogen atom or a $C_1$-$C_6$ alkyl group;
   X represents a heteroatom selected from the group consisting of oxygen and sulfur, and a divalent group of —N($R_6$)—, with $R_6$ representing a hydrogen atom or a $C_1$-$C_6$ alkyl group;
   ---- represents a single or double bond;
   n is 1, 2 or 3; and with the proviso that, when $R_3$ and $R_4$ form an oxo group via carbon atoms of $R_3$ and $R_4$ and X represents an oxygen atom, $R_1$ is not a hydroxymethyl group.

8. A process for coloring skin comprising:
topically applying to the skin in need of coloring, or orally administering to a person having skin in need of coloring, a composition comprising, in a physiologically acceptable medium, a coloring effective amount of at least one cannabinoid compound of formula (I):

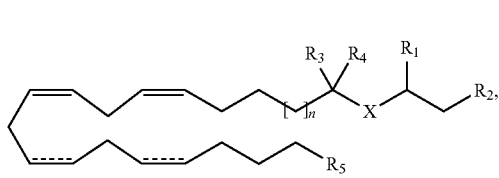

(I)

a geometric isomer thereof, an optical isomer thereof, a cosmetically acceptable acid or base salt thereof, or a hydrate thereof,
wherein
$R_1$ represents a hydrogen atom, or a $C_1$-$C_{30}$ alkyl group, which is optionally substituted with a hydroxyl (OH) group;
$R_2$ represents a halogen atom or a group selected from the group consisting of a hydroxyl group, a thiol (SH) group, and an amino group optionally substituted with one or two $C_1$-$C_6$ alkyl groups;
$R_3$ and $R_4$ form an oxo group via carbon atoms of $R_3$ and $R_4$ or else $R_3$ and $R_4$ represent a hydrogen atom;
$R_5$ represents a hydrogen atom or a $C_1$-$C_6$ alkyl group;
X represents a heteroatom selected from the group consisting of oxygen and sulfur, and a divalent group of —N($R_6$)—, with $R_6$ representing a hydrogen atom or a $C_1$-$C_6$ alkyl group;
---- represents a single or double bond;
n is 1, 2 or 3; and
with the proviso that, when $R_3$ and $R_4$ form an oxo group via carbon atoms of $R_3$ and $R_4$ and X represents an oxygen atom, $R_1$ is not a hydroxymethyl group.

9. A process for treating natural whitening of head hair comprising:
topically applying to head hair in need of coloring, or orally administering to a person having hair in need of coloring, a composition comprising, in a physiologically acceptable medium, a coloring effective amount of at least one cannabinoid compound of formula (I):

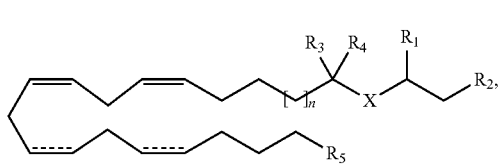

(I)

a geometric isomer thereof, an optical isomer thereof, a cosmetically acceptable acid or base salt thereof, or a hydrate thereof,
wherein
$R_1$ represents a hydrogen atom, or a $C_1$-$C_{30}$ alkyl group, which is optionally substituted with a hydroxyl (OH) group;

$R_2$ represents a halogen atom or a group selected from the group consisting of a hydroxyl group, a thiol (SH) group, and an amino group optionally substituted with one or two $C_1$-$C_6$ alkyl groups;
$R_3$ and $R_4$ form an oxo group via carbon atoms of $R_3$ and $R_4$ or else $R_3$ and $R_4$ represent a hydrogen atom;
$R_5$ represents a hydrogen atom or a $C_1$-$C_6$ alkyl group;
X represents a heteroatom selected from the group consisting of oxygen and sulfur, and a divalent group of —N($R_6$)—, with $R_6$ representing a hydrogen atom or a $C_1$-$C_6$ alkyl group;
---- represents a single or double bond;
n is 1, 2 or 3; and
with the proviso that, when $R_3$ and $R_4$ form an oxo group via carbon atoms of $R_3$ and $R_4$ and X represents an oxygen atom, $R_1$ is not a hydroxymethyl group.

10. The process of claim 8, wherein the cannabinoid compound is present at a concentration of from 0.00001% to 10% by weight, relative to a total weight of the composition.

11. The process of claim 8, wherein the cannabinoid compound is selected from the group consisting of anandamide, methanandamide, arachidonyl-2'-chloroethylamide, linoleyl ethanolamide, docosatetraenyl ethanolamide and 2-arachidonyl glyceryl ether.

12. The process of claim 9, wherein the cannabinoid compound is present at a concentration of from 0.00001% to 10% by weight, relative to a total weight of the composition.

13. The process of claim 9, wherein the cannabinoid compound is selected from the group consisting of anandamide, methanandamide, arachidonyl-2'-chloroethylamide, linoleyl ethanolamide, docosatetraenyl ethanolamide and 2-arachidonyl glyceryl ether.

14. A process for treating skin having vitiligo or *pityriasis versicolor* comprising: applying to skin in need of treatment for vitiligo or *pityriasis versicolor* a composition comprising a vitiligo or *pityriasis versicolor* treating effective amount of at least one cannabinoid compound of formula (I):

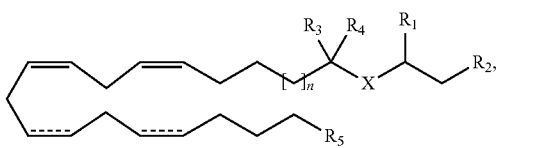

(I)

a geometric isomer thereof, an optical isomer thereof, a cosmetically acceptable acid or base salt thereof, or a hydrate thereof,
wherein
$R_1$ represents a hydrogen atom, or a $C_1$-$C_{30}$ alkyl group, which is optionally substituted with a hydroxyl (OH) group;
$R_2$ represents a halogen atom or a group selected from the group consisting of a hydroxyl group, a thiol (SH) group, and an amino group optionally substituted with one or two $C_1$-$C_6$ alkyl groups;
$R_3$ and $R_4$ form an oxo group via carbon atoms of $R_3$ and $R_4$ or else $R_3$ and $R_4$ represent a hydrogen atom;
$R_5$ represents a hydrogen atom or a $C_1$-$C_6$ alkyl group;
X represents a heteroatom selected from the group consisting of oxygen and sulfur, and a divalent group of —N($R_6$)—, with $R_6$ representing a hydrogen atom or a $C_1$-$C_6$ alkyl group;
---- represents a single or double bond;

n is 1, 2 or 3; and with the proviso that, when $R_3$ and $R_4$ form an oxo group via carbon atoms of $R_3$ and $R_4$ and X represents an oxygen atom, $R_1$ is not a hydroxymethyl group to a patient in need thereof.

15. The process of claim 14, wherein the cannabinoid compound is selected from the group consisting of anandamide, methanandamide, arachidonyl-2'-chloroethylamide, linoleyl ethanolamide, docosatetraenyl ethanolamide and 2-arachidonyl glyceryl ether.

* * * * *